United States Patent [19]

Khare

[11] Patent Number: 5,202,519

[45] Date of Patent: Apr. 13, 1993

[54] ISOMERIZATION PROCESS AND CATALYST THEREFOR

[75] Inventor: Gyanesh P. Khare, Bartlesville, Okla.

[73] Assignee: Phillips Petroleum Company, Bartlesville, Okla.

[21] Appl. No.: 941,360

[22] Filed: Sep. 4, 1992

[51] Int. Cl.$^5$ .............................................. C07C 5/13
[52] U.S. Cl. .................................. 585/741; 585/747; 585/748
[58] Field of Search ........................ 585/741, 747, 748

[56] References Cited

U.S. PATENT DOCUMENTS

| | | |
|---|---|---|
| 2,820,074 | 1/1958 | Pines . |
| 3,238,272 | 3/1966 | Nixon . |
| 3,248,343 | 4/1966 | Kelly et al. . |
| 3,420,909 | 1/1969 | Schmerling . |
| 3,502,735 | 3/1970 | Copelin . |
| 3,631,211 | 12/1971 | Schmerling . |
| 3,655,797 | 4/1972 | Schmerling . |
| 3,760,021 | 9/1973 | Boggs ................................. 585/460 |
| 3,846,503 | 11/1974 | Schmerling et al. . |
| 5,012,025 | 4/1991 | Sankaran ............................. 585/442 |
| 5,104,846 | 4/1992 | Sankaran ............................. 502/355 |

OTHER PUBLICATIONS

N. Kitajima, "Two Component Friedel–Crafts Catalysts as Solids Superacids", Materials Chemistry and Physics 17 (1987), pp. 31–48.

N. Kitajima et al., "Cu(AlCl$_4$)$_2$ as a Catalyst for the Isomerization of Pentane at Room Temperature", Journal of Molecular Catalysis 10 (1981), pp. 121–122.

Y. Ono et al., "Isomerization of Pentane with AlCl$_3$–CuSO$_4$ Mixtures", Journal of Catalysis 64 (1980), pp. 13–17.

N. Kitajima et al., "On the Active Species of Aluminum(III) Bromide–Copper(II) Bromide Mixtures as Catalysts for the Isomerization of Pentane", Journal Chem. Society, Perkin Transactions II, 1980, pp. 1201–1205.

Y. Ono et al., "Isomerization of Pentane with Aluminum Chloride (Gallium Chloride) –Cupric Salt Complexes", Proceedings 7th Internat. Congress Catalys., Tokyo, 1980, pp. 1006–1017.

Y. Ono et al., "Highly Selective Isomerization of Pentane with AlBr$_3$–Metal Sulfate Mixtures", Chemistry Letters, 1978, pp. 1061–1064.

*Primary Examiner*—Patrick P. Garvin
*Assistant Examiner*—E. D. Irzinski
*Attorney, Agent, or Firm*—K. K. Brandes

[57] ABSTRACT

A catalyst composition is prepared by mixing at least an aluminum halide (preferably AlCl$_3$), at least one copper(II) salt (preferably CuCl$_2$), calcium aluminate and at least one alcohol (preferably ethanol), shaping the mixture, and drying the shaped particles. The thus-obtained catalyst composition is employed in the isomerization of alkanes and/or cycloalkanes.

11 Claims, No Drawings

ISOMERIZATION PROCESS AND CATALYST THEREFOR

BACKGROUND OF THE INVENTION

In one aspect, this invention relates to the preparation of a composition of matter which is effective as a catalyst for isomerizing alkanes and cycloalkanes. In another aspect, this invention relates to an alkane/cycloalkane isomerization process.

The use of combinations of aluminum halide (in particular $AlCl_3$) and certain metal chlorides and sulfates (in particular $CuCl_2$ or $CuSO_4$) for alkane isomerization is known and has been described in various scientific articles. The present invention is directed to a novel, effective alkane isomerization catalyst composition comprising a combination of aluminum halide(s) and copper(II) salt(s) and a particular solid inorganic refractory material.

SUMMARY OF THE INVENTION

It is an object of this invention to provide a method of preparing a catalyst composition from aluminum halide(s), copper(II) salt(s) and a solid inorganic support material. It is another object of this invention to provide a catalyst composition prepared by this process. It is a further object of this invention to employ this catalyst composition in a process for isomerizing alkanes and/or cycloalkanes. Other objects and advantages will be apparent from the detailed description of the invention and the appended claims.

In accordance with this invention, a method of preparing a composition of matter (effective as an alkane and/or cycloalkane isomerization catalyst composition) comprises the steps of:

(a) mixing, in the substantial absence of water, at least one aluminum halide selected from the group consisting of $AlCl_3$ and $AlBr_3$, at least one copper(II) salt, calcium aluminate and at least one alcohol containing 1-12 carbon atoms per molecule, at a molar ratio of said at least one aluminum halide to said at least one copper(II) salt in excess of about 1:1;

(b) shaping the mixture obtained in step (a); and (c) removing said at least one alcohol from the shaped particles obtained in step (b) so as to obtain dry shaped particles.

Preferably, the at least one aluminum halide is aluminum chloride and the at least one copper(II) salt is cupric chloride. Also preferably, the at least one alcohol is ethanol. The preferred molar ratio of $AlCl_3$ to $CuCl_2$ is about 2:1 to about 3:1. The preferred shaping method of step (b) is extrusion.

Also in accordance with this invention, a composition of matter prepared by the above-described method is provided.

Further in accordance with this invention, a process for isomerizing saturated hydrocarbons comprises contacting at least one feed hydrocarbon selected from the group consisting of alkanes containing 4-10 carbon atoms per molecule and cycloalkanes containing 5-10 carbon atoms per molecule with the catalyst composition having been prepared by the above-described preparation method, at such contacting conditions as to convert at least a portion of said at least one feed hydrocarbon to at least one product isomer (having the same number of carbon atoms per molecule as said at least one feed hydrocarbon but having a different structural formula). When the feed hydrocarbon is an alkane, concurrently with the isomerization of a portion of the feed alkane, another portion of said feed alkane is generally disproportionated, i.e., converted to a mixture of at least one alkane having a higher number of carbon atoms per molecule and at least one alkane having a lower number of carbon atoms per molecule than said feed alkane(s). Presently preferred feed hydrocarbons are normal (straight-chain) $C_5-C_8$ alkanes, branched $C_5-C_8$ alkanes (isoalkanes) and methyl-substituted $C_5-C_7$ cycloalkanes.

DETAILED DESCRIPTION OF THE INVENTION

Mixing step (a) in the preparation method of this invention can be carried out in any suitable manner by any suitable, conventional mixing means in the substantial absence of moisture. Non-limiting examples of suitable, essentially anhydrous Cu(II) salts are $CuCl_2$ (most preferred), $CuBr_2$, $CuI_2$, $CuSO_4$, $Cu(HSO_4)_2$ and $Cu(NO_3)_2$. Suitable, essentially anhydrous alcohols which can be employed include (but are not limited to) methanol, ethanol (most preferred), 1-propanol, 2-propanol, isopropanol, butanols, pentanols and hexanols.

Generally, the molar ratio of aluminum halide(s) to copper(II) salt(s) is about 2:1 to about 5:1 (preferably about 2:1 to about 3:1), the ratio of the weight of calcium aluminate to the combined weight of aluminum halide(s) and copper(II) salt(s) is about 0.01:1 to about 0.5:1, and the ratio of the weight of alcohol(s) to the combined weight of aluminum halide(s), Cu(II) salt(s) and Ca aluminate is about 0.01:1 to about 0.1:1. It is within the scope of this invention (yet presently not preferred) to have other ingredients present in step (a), such as $AlI_3$, $Al_2(SO_4)_3$, calcium silicate cement, $GaCl_3$, and compounds (in particular chlorides and sulfates) of Ti, Zr, Hf, Ta, Cr, Mo, Fe, Co and Ni.

Shaping step (b) can be carried out in any suitable manner, such as by extrusion through one die or a plurality of dies, or by pelletizing (e.g., in a rotary mixer) or by tabletting (in a suitable press), preferably in the substantial absence of moisture. Generally, the size of the obtained shaped particles (i.e., the diameter of extruded cylinders or of pellets) is about 0.1-2 cm.

Drying step (c) can be carried out in any suitable manner, preferably in the substantial absence of moisture at a temperature of about 50°-350° C. for a time period of about 0.1-20 hours, more preferably under vacuum conditions (i.e., at a pressure of below 1 atm) and/or in an inert gas atmosphere (e.g., $N_2$ or He or Ar). The dried particles are preferably allowed to cool in a dry inert gas atmosphere.

Also in accordance with this invention, the catalyst composition described above is employed for at least partially isomerizing normal (straight-chain) alkanes and/or isoalkanes (i.e., branched alkanes) containing 4-10 carbon atoms per molecule and/or cycloalkanes containing 5-10 carbon atoms. When alkanes (in particular branched alkanes) are employed as feed hydrocarbons, a substantial portion of the feed hydrocarbons is generally disproportionated (concurrently with the isomerization). Non-limiting examples of suitable feed alkanes are n-butane, isobutane, n-pentane, isopentane (i.e., 2-methylbutane), n-hexane, isohexanes (such as 2-methylpentane, 3-methyl-pentane, 2,2-dimethylbutane), n-heptane, isoheptanes (in particular methyl-substituted hexanes and dimethyl-substituted pentanes), n-octane, isooctanes (in particular methyl-substituted heptanes and dimethyl-substituted hexanes), n-nonane, isononanes (in particular methyl-substituted octanes, dimethyl-substituted heptanes, trimethyl-substituted hexanes), n-decane and isodecanes (in particular methyl-substituted nonanes, dimethyl-substituted octanes, trimethyl-substituted heptanes, tetramethyl-substituted hexanes). Presently preferred feed alkanes are $C_4$-$C_8$ normal alkanes and $C_4$-$C_8$ isoalkanes. When the primary objective of the process of this invention is to make highly branched alkanes by isomerization, preferably normal (straight-chain) and monomethyl-substituted feed alkanes are used. However, when the objective of the process of this invention is to primarily disproportionate the feed alkanes (i.e., convert them to higher and lower alkanes), preferably branched feed alkanes are used. Presently preferred feed alkanes are n-pentane, and 2,2,4-trimethylpentane (isooctane).

Non-limiting examples of suitable feed cycloalkanes are methylcyclobutane, methylcyclopentane (particularly preferred), methylcyclohexane, dimethylcyclopentanes, dimethylcyclohexanes, trimethylcyclopentanes, methylcycloheptane, dimethylcycloheptanes and trimethylcyclohexanes. Cycloalkanes generally do not disproportionate to any significant extent under the operating conditions of the isomerization process of this invention.

The process for isomerizing $C_4$-$C_{10}$ alkanes and/or $C_5$-$C_{10}$ cycloalkanes with the above-described catalyst composition can be carried out at any suitable reaction conditions, generally at a temperature of up to about 300° C., preferably at about 20°-100° C., more preferably at about 20°-40° C., generally at a pressure of about 1-200 atm. The feed alkane(s) and/or cycloalkane(s) can be contacted with the catalyst composition in any suitable mode, such as in a slurry-type operation with the catalyst being dispersed in the feed hydrocarbon(s), or in a fixed catalyst bed operation in which the hydrocarbon feed flows upward or downward through a solid catalyst layer (or several catalyst layers), generally at a liquid hourly space velocity of about 0.1-10 cc hydrocarbon feed per cc catalyst per hour. The time of contact between the feed alkane(s) and/or cycloalkane(s) and the catalyst composition generally is in the range of about 5 minutes to about 24 hours, preferably about 0.5-6 hours. The isomerization process can be carried out as a batch operation or as a continuous operation.

The isomerization processes of this invention frequently generates a multitude of products, especially in the case of alkanes which do not only isomerize but also, to a significant extent, disproportionate to higher and lower alkanes. Thus, it is generally necessary to separate the various formed hydrocarbon products from one another and from unconverted feed hydrocarbon(s). This separation can be carried out in any suitable manner, generally by fractional distillation (optionally in the presence of an extractant, i.e., by extractive distillation), as is easily determined by persons skilled in the various liquid-liquid separation technologies.

The following examples are provided to further illustrate the processes of this invention, and are not to be construed as unduly limiting the scope of this invention.

EXAMPLE I

This example illustrates the preparation of various isomerization catalyst compositions from $AlCl_3$ and $CuCl_2$.

Catalyst A (Control) was prepared by manually mixing 100 grams of $AlCl_3$, 50 grams of $CuCl_2$ and 4.5 mL of dry ethanol, and extruding the mixture through a laboratory extruder equipped with an aluminum die plate having twelve 1/16 inch holes. Both preparation steps were carried out in a glove bag under a dry nitrogen atmosphere. The obtained extrudates were dried for 7 hours under vacuum conditions at 65°-70° C., followed by a dry nitrogen gas purge. The average crush strength of the dry extrudates, measured on a laboratory crush strength apparatus equipped with two metal plates of ⅛ inch diameter and a 0-30 lb. force gauge, was 5.8 lb. per particle.

Catalyst B (Control) was prepared by manually mixing 80 grams of $AlCl_3$, 40 grams of $CuCl_2$, 30 grams of gamma-alumina (provided by Degussa Corporation, Allendale, N.J., under the product designation of Aluminum Oxide C) and 5 mL of dry ethanol in a glove bag under a dry nitrogen gas atmosphere. The mixture was extruded and dried, essentially in accordance with the procedure described for Catalyst A. The average crush strength of Catalyst B extrudates was 9.3 lb. per particle.

Catalyst C (Invention) was prepared by manually mixing 100 grams (about 0.75 mole) of $AlCl_3$, 40 grams (about 0.30 mole) of $CuCl_2$, 7 grams of calcium aluminate (provided by Lafarge Calcium Aluminates, Chesapeake, Va., under the product designation of Secar 71) and 5 mL of dry ethanol. The mixture was extruded through a ¼" aluminum die plate containing ten 1/16 inch holes. Both preparation steps were carried out in a glove bag under a dry nitrogen atmosphere. The extrudates were dried overnight at 150° C. under vacuum conditions, followed by a dry nitrogen gas purge. The average crush of Catalyst C particles was 1.7 lb. per particle.

EXAMPLE II

This example illustrates the performance of the catalysts described in Example I for the conversion of a normal alkane.

In one test series, 2 mL n-pentane and 1.0 grams of Catalysts A, B and C were placed in sealed glass tubes at about 24° C. Samples of the liquid reaction mixture were withdrawn at certain time intervals and analyzed by means of a conventional gas chromatograph. Test results are summarized in Table I.

TABLE I

| Catalyst | Reaction Time (Hours) | % Conversion of n-Pentane |
| --- | --- | --- |
| A (Control) | 1 | 1.6 |
|  | 4 | 35.5 |
|  | 24 | 82.0 |
| B (Control) | 1 | 2.5 |
|  | 4 | 5.7 |
|  | 24 | 12.0 |
| C (Invention) | 1 | 71.5 |
|  | 4 | 92.0 |
|  | 24 | 95.5 |

The above test data clearly show the superiority of invention Catalyst C containing Ca aluminate over the two other $AlCl_3/CuCl_2$-containing catalysts. In all three test runs, the formed product hydrocarbons were primarily isopentane (2-methylbutane) and isohexanes (2,2-dimethylbutane, 2-methylpentane, 3-methylpentane). Smaller amounts of other identified hydrocarbon products were those of isobutane, isoheptanes (in particular 2,2 and 2,4-dimethylpentanes, 3-ethylpentane and 2-methylhexane) and $C_{7+}$ alkanes. Thus, while a substantial portion of n-pentane was isomerized to isopentane, an even greater portion of the feed n-pentane had been converted to $C_6$, $C_{7+}$ and $C_4$ alkanes (probably by a combination of disproportionation, cracking and alkylation reactions).

EXAMPLE III

This example illustrates the performance of the catalysts described in Example I for the conversion of an isoalkane. 10 mL of an isoalkane (2,2,4-trimethylpentane) and 5 grams of Catalysts A, B and C were placed in a sealed glass tube at about 24° C. Samples of the reaction mixture were withdrawn after 1 hour and analyzed by means of a gas chromatograph. Test results are summarized in Table II.

TABLE II

| Catalyst | Reaction Time (Hours) | % Conversion of Isooctane |
| --- | --- | --- |
| A (Control) | 1 | 34.5 |
| B (Control) | 1 | 3.0 |
| C (Invention) | 1 | 54.6 |

Test results in Table II clearly demonstrate the superiority of Catalyst C over Catalysts A and B. In all three test runs, the reaction product contained unconverted feed isooctane (i.e., 2,2,4-trimethylpentane), other isooctanes (in particular 2,3-, 2,4- and 2,5-dimethylhexane and trimethylpentanes), isononanes (in particular trimethylhexanes and dimethylheptanes), and $C_4$-$C_7$ isoalkanes (in particular isobutane, 2-methylbutane, 2,4-dimethylbutane, 2,4-dimethylpentane and 2-methylhexane). Thus, besides the isomerization of the feed isooctane to other $C_8$ isomers, a substantial portion of the feed isooctanes had been converted to higher and lower isoalkanes (probably by a combination of disproportionation, cracking and alkylation reactions).

EXAMPLE IV

This example illustrates the performance of the catalysts described in Example I for the conversion of methylcyclopentane to cyclohexane at about 23° C., essentially in accordance with the procedure described in Example II. Test results summarized below in Table III demonstrate the superiority of Invention Catalyst C.

TABLE III

| Catalyst | Reaction Time (Hours) | % Conversion of Methylcyclopentane |
| --- | --- | --- |
| A (Control) | 1 | 0.7 |
|  | 4 | 1.3 |
|  | 24 | 12.8 |
| B (Control) | 1 | 1.5 |
|  | 4 | 7.3 |
|  | 24 | 22.4 |
| C (Invention) | 1 | 65.8 |
|  | 4 | 87.3 |
|  | 24 | 90.1 |

Note:
The formed products consisted essentially of cyclohexane.

Reasonable variations, modifications and adaptations for various conditions and reactants can be made within the scope of the disclosure and the appended claims without departing from the scope of this invention.

That which is claimed is:

1. A process for isomerizing saturated hydrocarbons comprising contacting at least one feed hydrocarbon selected from the group consisting of alkanes containing 4-10 carbon atoms per molecule and cycloalkanes containing 5-10 carbon atoms per molecule with a catalyst composition at a temperature of up to about 300° C., at such contacting conditions as to convert said at least one feed hydrocarbon to at least one product isomer; wherein said catalyst composition has been prepared by a method comprising the steps of:
   (a) mixing at least one aluminum halide selected from the group consisting of $AlCl_3$ and $AlBr_3$ with at least one copper(II) salt, calcium aluminate and at least one alcohol containing 1-12 carbon atoms per molecule, at a molar ratio of said at least one aluminum halide to said at least one alcohol in excess of about 1:1;
   (b) shaping the mixture obtained in step (a); and
   (c) removing said at least one alcohol from the shaped particles obtained in step (b) so as to obtain dry shaped particles.

2. A process in accordance with claim 1, wherein said at least one aluminum halide is $AlCl_3$, said at least one copper(II) salt is $CuCl_2$, said at least one alcohol is ethanol, and step (a) is carried out in the substantial absence of moisture.

3. A process in accordance with claim 2, wherein the molar ratio of $AlCl_3$ to $CuCl_2$ is about 2:1 to about 5:1, the ratio of the weight of calcium aluminate to the combined weight of $AlCl_3$ and $CuCl_2$ is about 0.01:1 to about 0.5:1, and the ratio of the weight of ethanol to the combined weight of $AlCl_3$, $CuCl_2$ and calcium aluminate is 0.01:1 to about 0.1:1.

4. A process in accordance with claim 2, wherein shaping step (b) is extrusion in the substantial absence of moisture, and step (c) is carried out at a temperature of about 50°-350° C. in the substantial absence of moisture.

5. A process in accordance with claim 2, wherein said contacting conditions comprise a temperature of about 20°-100° C., a pressure of about 1-200 atmospheres, and a time of contact between said at least one feed hydrocarbon and said catalyst composition of about 5 minutes to about 24 hours.

6. A process in accordance with claim 5, wherein said at least one feed hydrocarbon is at least one straight-chain alkane.

7. A process in accordance with claim 6, wherein said at least one straight-chain alkane is n-pentane.

8. A process in accordance with claim 5, wherein said at least one feed hydrocarbon is at least one branched alkane.

9. A process in accordance with claim 8, wherein said at least one branched alkane is 2,2,4-trimethylpentane.

10. A process in accordance with claim 5, wherein said at least one feed hydrocarbon is methylcyclopentane.

11. A process in accordance with claim 1, comprising the additional step of separating said at least one product isomer from unconverted feed and from other hydrocarbon products.

* * * * *